(12) United States Patent
Laster et al.

(10) Patent No.: US 11,322,250 B1
(45) Date of Patent: May 3, 2022

(54) INTELLIGENT MEDICAL CARE PATH SYSTEMS AND METHODS

(71) Applicant: TNacity Blue Ocean LLC, Memphis, TN (US)

(72) Inventors: Scott K Laster, Memphis, TN (US); Brian D. Childress, Richardson, TX (US)

(73) Assignee: Tnacity Blue Ocean LLC

( * ) Notice: Subject to any disclaimer, the term of this patent is extended or adjusted under 35 U.S.C. 154(b) by 0 days.

(21) Appl. No.: 17/079,501

(22) Filed: Oct. 25, 2020

Related U.S. Application Data

(60) Provisional application No. 62/925,979, filed on Oct. 25, 2019.

(51) Int. Cl.
*G16H 20/17* (2018.01)
*G16H 40/20* (2018.01)
(Continued)

(52) U.S. Cl.
CPC .......... *G16H 40/20* (2018.01); *A61B 5/0022* (2013.01); *A61B 5/0205* (2013.01); *A61B 5/02055* (2013.01); *A61B 5/14532* (2013.01); *A61B 5/14551* (2013.01); *A61B 5/369* (2021.01); *A61B 5/4806* (2013.01); *A61B 5/4845* (2013.01); *A61B 5/4848* (2013.01); *A61B 5/681* (2013.01); *A61B 5/686* (2013.01); *A61B 5/7275* (2013.01); *G06Q 10/06316* (2013.01); *G06Q 10/10* (2013.01); *G06Q 50/01* (2013.01); *G16H 10/60* (2018.01); *G16H 15/00* (2018.01); *G16H 20/13* (2018.01); *G16H 40/67* (2018.01); *G16H 50/20* (2018.01); *G16H 50/70* (2018.01);
(Continued)

(58) Field of Classification Search
CPC ........ G16H 40/20; G16H 40/67; G16H 10/60; G16H 15/00; G16H 50/70; G16H 50/20; G16H 20/13; G16H 80/00; G06Q 10/06316; G06Q 10/10; G06Q 50/01; G06Q 40/08; G06Q 50/26; G06F 40/174; A61B 5/0022; A61B 5/0205; A61B 5/02055; A61B 5/14532; A61B 5/14551; A61B 5/369; A61B 5/4806; A61B 5/4845; A61B 5/4848; A61B 5/681; A61B 5/686; A61B 5/7275; A61B 5/021; A61B 5/024; A61B 5/0245; A61B 5/0533; A61B 5/082; A61B 5/091
See application file for complete search history.

(56) References Cited

U.S. PATENT DOCUMENTS 8,126,736 B2   2/2012   Anderson et al.
8,423,180 B1 * 4/2013   Frederick ................ G07F 9/026
                                                       700/236
(Continued)

*Primary Examiner* — Maroun P Kanaan
(74) *Attorney, Agent, or Firm* — Veritay Group IP, PLLC; Susan B. Fentress; Liam O'Donnell

(57) ABSTRACT

Further system and methods associated there with can use a combination of big data, machine learning, and/or regression equations to make living care paths based on sensitivities, probability, and/or statistics, which increases the chances of a living care path being successful. System, in some embodiments, can also provide a visual representation of the treatment options and statistics to the patient and HCP. As configured, system can empower patients, making them more informed about their condition, expectations of recovery, and more confident in their HCP's recommended treatment measure.

4 Claims, 14 Drawing Sheets

(51) Int. Cl.
*G16H 50/70* (2018.01)
*G16H 50/20* (2018.01)
*G16H 15/00* (2018.01)
*G06Q 50/00* (2012.01)
*G06Q 10/06* (2012.01)
*G06Q 10/10* (2012.01)
*G16H 20/13* (2018.01)
*G16H 40/67* (2018.01)
*G16H 80/00* (2018.01)
*A61B 5/00* (2006.01)
*A61B 5/0205* (2006.01)
*A61B 5/1455* (2006.01)
*A61B 5/145* (2006.01)
*G16H 10/60* (2018.01)
*A61B 5/369* (2021.01)
*G06F 40/174* (2020.01)
*G06Q 40/08* (2012.01)
*G06Q 50/26* (2012.01)
*A61B 5/021* (2006.01)
*A61B 5/024* (2006.01)
*A61B 5/0245* (2006.01)
*A61B 5/08* (2006.01)
*A61B 5/0533* (2021.01)
*A61B 5/091* (2006.01)

(52) U.S. Cl.
CPC .............. *G16H 80/00* (2018.01); *A61B 5/021* (2013.01); *A61B 5/024* (2013.01); *A61B 5/0245* (2013.01); *A61B 5/0533* (2013.01); *A61B 5/082* (2013.01); *A61B 5/091* (2013.01); *G06F 40/174* (2020.01); *G06Q 40/08* (2013.01); *G06Q 50/26* (2013.01)

(56) References Cited

U.S. PATENT DOCUMENTS

| | | |
|---|---|---|
| 9,129,054 B2 | 9/2015 | Nawana et al. |
| 9,324,022 B2 | 4/2016 | Williams, Jr. et al. |
| 9,894,498 B2 | 2/2018 | Snellenberg |
| 10,729,907 B2 | 8/2020 | Arcot et al. |
| 10,748,644 B2 | 8/2020 | Shriberg et al. |
| 10,783,988 B1 | 9/2020 | Atkin |
| 10,784,000 B2 | 9/2020 | Wu et al. |
| 2003/0069756 A1* | 4/2003 | Higginbotham ........ G16H 40/20 705/2 |
| 2015/0019241 A1 | 1/2015 | Bennett et al. |
| 2017/0124261 A1* | 5/2017 | Mari ................. G06Q 10/1095 |
| 2017/0161437 A1* | 6/2017 | Weinstein ............. G16H 70/20 |
| 2017/0262604 A1* | 9/2017 | Francois ................ G16H 50/20 |
| 2019/0034591 A1 | 1/2019 | Mossin et al. |
| 2019/0228848 A1* | 7/2019 | Saliman ................ G16H 10/20 |
| 2019/0252079 A1* | 8/2019 | Constantin ......... A61B 5/14532 |
| 2020/0143922 A1* | 5/2020 | Chekroud ............ G06K 9/6218 |
| 2020/0273578 A1* | 8/2020 | Kutzko .................. G06N 5/025 |
| 2020/0273581 A1* | 8/2020 | Wolf .................... A61B 90/361 |

* cited by examiner

INTELLIGENT MEDICAL CARE PATH SYSTEMS AND METHODS

RELATED APPLICATIONS

This application claims priority to Provisional Patent Application No. 62/925,979 filed Oct. 25, 2019 the entire disclosure of which is hereby incorporated by reference in its entirety.

TECHNICAL FIELD

The presently disclosed subject matter relates to a system and method to optimize a patient's care path.

BACKGROUND OF THE INVENTION

Existing approaches for selecting and implementing a patient care path suffer from a number of disadvantages.

For example, while health care providers (HCP) are often skilled medical professionals who receive constant training and updates to the latest medical procedures, not all HCPs use the same approaches to diagnose and treat patients. Lack of standardization in diagnosis and treatment can be attributable to variations in training, participation, and willingness of HCPs to adopt different approaches. Further, even when using similar approaches, many techniques for diagnosing ailments, determining when to initiate treatment, determining which treatment to provide, how aggressively to treat the ailment, adjustment of treatment over time, and similar considerations are often based on subjective criteria, thus leading to a further lack of standardization and objectivity amongst HCPs. As a result, patients can be less inclined to trust a diagnosis, ongoing treatment, or care path prescribed by an HCP and thus fail to fully engage in the prescribed care path to the detriment of the patient's health. Further, HCPs can falsely believe or perhaps be unsure whether they will be reimbursed by insurers/government programs for certain treatments and thus either take a loss or stray from recommending a particular treatment for fear of not being reimbursed.

Further, existing approaches often result in frequent patient visits to an HCP's office to monitor the patient's health. These visits are often time consuming. For example, patients often spend significant time filling out paperwork relating to medical history, updates since their last visit, and insurance or payment methods. Another time-consuming task is when HCPs describe treatment measures and discuss charts with patients. Each contributes to inefficiencies from a patient care and cost standpoint and can contribute to a lack of available historical data (e.g., historical progress of pain level, pain duration, etc.) that could otherwise be helpful to an HCP in making informed decisions when diagnosing and treating the patient.

Determining when medical issues become severe enough to warrant a change in a patient's health care plan is another problem. Existing approaches often rely on frequent and often unnecessary office visits so that an HCP can monitor changes in the patient's condition, as well as on self-reporting by the patient, to the best of their memory, when he/she believes there has been a change of note. Such approaches are stricken with inefficiencies and subjectivity, especially on the part of the patient who can be inclined to either believe, on the one hand, that everything is significant or, on the other hand, overlooks or otherwise fails to report changes of significance—whether purposefully or by accident.

Therefore, there is a need for improved approaches for selecting and implementing a patient care.

BRIEF SUMMARY OF THE INVENTION

One novel aspect of the present inventive subject matter includes a non-transitory computer-readable medium storing instruction that, when executed on a computing device, cause the computing device to perform a method for providing a patient's living care path. This method includes the steps of: receiving patient related data from one or more data sources; aggregating a plurality of medical data sets from one or more data sources into one or more phenotypic groups to assign at least one phenotypic group; first processing the plurality of medical data set of the at least one assigned phenotypic group to predict one or more patient outcomes; second processing the plurality of medical data set of the assigned phenotypic group to determine an optimal time based set of measures for increasing the probability of attaining an at least one living care path goal; processing the one or more patient outcomes and the optimal time based set of measures for providing the living care path; and providing a graphical user interface showing the living care path, wherein the graphical user interface shows: the differential between the living care path and present performance and a plurality of measures to alter this differential.

Another novel aspect of the present inventive subject matter includes a computing system for providing a patient's living care path. This system includes: a computing device, made of a transceiver that communicates over a network; a memory that store at least one instruction; and a processor that executes instructions that perform action, including receiving patient related data from one or more data sources; aggregating a plurality of medical data sets from one or more data sources into one or more phenotypic groups to assign at least one phenotypic group; first processing the plurality of medical data set of the at least one assigned phenotypic group to predict one or more patient outcomes; second processing the plurality of medical data set of the assigned phenotypic group to determine an optimal time-based set of measures for increasing the probability of attaining an at least one living care path goal; and processing said one or more patient outcomes and said optimal time-based set of measures for providing the living care path; and a graphical user interface to provide said living care path.

Another novel aspect of the present inventive subject matter includes a patient hub apparatus. This apparatus can include: an electronic circuitry made of a processor operably coupled to a memory and a power source, wherein the memory stores computer executable instructions and a processor that executes the instructions to cause the patient hub apparatus to provide a medication and to display the patient's living care path, and at least one electronic communication connectivity device; an at least one data input device, wherein the one input device is a display; and housing defining a cavity having a medicine storage apparatus and a medicine dispensing apparatus, wherein the medicine storage apparatus is made of: a housing coupled to an at least one door and an at least one pin, wherein the at least one door is rotated by a torsion spring and the medicine dispensing apparatus is made of: a threaded rod, a coupler having internal threads, a linear actuating motor and a rotational motor.

BRIEF DESCRIPTION OF DRAWINGS

For a fuller understanding of the nature and desired objects of the present invention, reference is made to the following detailed description taken in conjunction with the accompanying drawing figures.

DETAILED DESCRIPTION OF INVENTION

Figure 1:
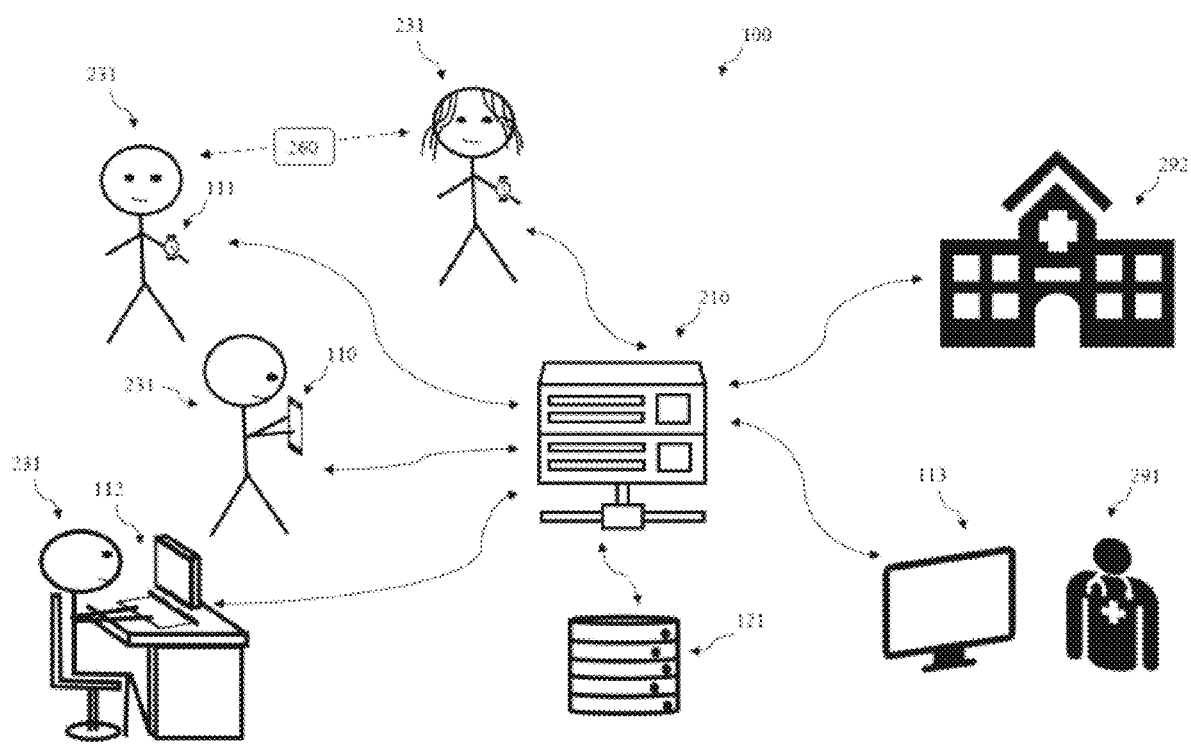
FIG. 1 depicts a schematic view of an intelligent medical care path system according to an embodiment of the present disclosure.

The present disclosure is directed to systems and methods for leveraging big data to optimize the medical diagnosis and treatment of individual patients. More specifically, systems and methods of the present disclosure are configured to provide a platform for collecting and aggregating healthcare information from a large population of patients and perform analytics on the data to identify trends in the outcomes of various care paths employed for patients with similar health issues, medical histories, demographics, and other characteristics that can affect the success of treatment. The present systems and methods can, in turn, use the information derived from these analytics to facilitate health care professionals (and patients as well) in determining, for similarly situated patients and/or conditions and/or outcome goals, etc., the optimal timing and types of treatment to provide in order to increase the chances of a successful outcome. To that end, systems and methods of the present disclosure can leverage electronic devices commonly used by patients in the course of their daily lives (e.g., wearables, mobile devices, tablets, computers, medical monitors (such as, EKG, Blood Glucose Monitors, and weight/BMI scale) to facilitate the collection of patient healthcare information both for aggregation, analysis, and patient monitoring. As configured, the present systems and methods help generate a robust pool of aggregated data that, in combination with enhanced patient monitoring (e.g. patient use and/or engagement of the app, health metrics, communications, etc.), allows health care professionals to: (i) standardize and/or personalize the diagnosis and treatment of patients across a large population, (ii) leverage predictive and prescriptive care decisions generated by the system to understand when a change in a patient's health warrants an intervention such as an office visit or the start of a particular treatment, etc. and (iii) optimize an individual patient's care path by recommending approaches that were successful for most similarly situated patients and/or diseases and providing continuous feedback on the respective patient's health and progress so that beneficial modifications can be made along the way. The present systems and methods can be configured to provide further benefits to patients, care-givers, support networks, and health care professionals by providing a customizable dashboard and automatic data population functionality to help health care professionals efficiently triage their visits and maximize opportunities for obtaining full reimbursement from insurance and government healthcare plans, as later described in more detail. As used herein, the term "patient" broadly includes any living creature and encompasses both humans and animals alike and is not intended to denote a level or state of health. As used herein, the term "health care professional" (HCP) broadly includes any person that is able to interpret health data (e.g. biometric, physiologic, co-morbidities, etc.), whether visual, analog, and/or digital in nature. Representative HCPs include medical doctors, surgeons, nurses, physicians' assistants, physical therapists, chiropractors, veterinarians, biologist, scientist, and the like. One of ordinary skill in the art will recognize other suitable caregivers and/or those involved in the caregiving process, such as family members, administrative personnel, and/or social workers, can be HCPs within the scope of the present disclosure. As used herein, the term "computing device," "mobile device," "mobile computing device," or "patient hub apparatus" broadly includes any electronic device capable of executing a computer program such as an application. Representative computing devices include desktop computers, servers, databases, mobile phones, smart phones, tablets, laptop computers, watches, drones, and the like. The term computing device can also include more specialized medical monitoring devices and can encompass consumer or specialized medical monitoring devices as paired with various instruments, sensors, and the like for collecting medical data. For example, the term medical monitoring device can envision as blood glucose level detectors, pacemakers, or other tools/instruments/sensors that a patient or health care professional can use or otherwise could be used to collect health data (e.g. biometric, physiologic, co-morbidities, etc.) for assessing a condition of a patient such as components for capturing images (e.g., a camera or image sensor), counting number of steps and/or type of movement (e.g., an accelerometer), determining heart rate (e.g., photodiode sensors, infrared LEDs, electrodes), determinizing body temperature (e.g., photoconductivity, infrared, thermistor, and/or optical sensors), transmitting data (e.g., radio signals, wire connection ports) and/or determining a location of the computing device (e.g., GPS functionality). In some embodiments a computing device is connected to a medical monitoring device. In some embodiments a medical monitoring device is capable of operation and/or transmitting data without being connected to a computing device. In some embodiments all processes are managed natively on a single portable device such as a smart phone etc. and data is never transmitted. Such an approach can be favorable from the standpoint of promoting compliance with privacy laws, such as HIPPA, since the data would remain on the device within the possession, custody, and control of the patient rather than transmitting the data over a network, where it could potentially be intercepted or accessed by an unauthorized person. In some embodiments, data is stored on portable devices (such as smart phone, etc.) and then, when connected to a network (cellular or internet, etc.), it transmits the data to the system via a transceiver.

FIG. 1 depicts a schematic view of an intelligent medical care path system 100 according to an embodiment of the present disclosure. As shown in FIG. 1, intelligent medical care path system 100, in various embodiments, can include various components including: a computing system 210, one or more internal and/or external databases 121, and a software application 238 (later shown in FIG. 2) configured to run on and/or in conjunction with one or more computing devices such as a mobile device or tablet 110, wearable device 111, or desktop or laptop computer 112. As shown, the computing system 210 can facilitate communication and/or data transfer between one or more patients 231 and one or more HCPs 291 and/or medical facilities 292. For example, in various embodiments, computing system 210 can facilitate the collection of patient information for aggregation and monitoring, notify HCPs of notable changes in patient healthcare information, request and schedule clinical appointments, and push changes in a patient's prescribed care path to a patient's mobile device, amongst other functionality as later described in more detail. In one embodiment, both the mobile device or tablet 110 and the computing system 210 can constitute a patient hub apparatus individually or together.

Figure 2:
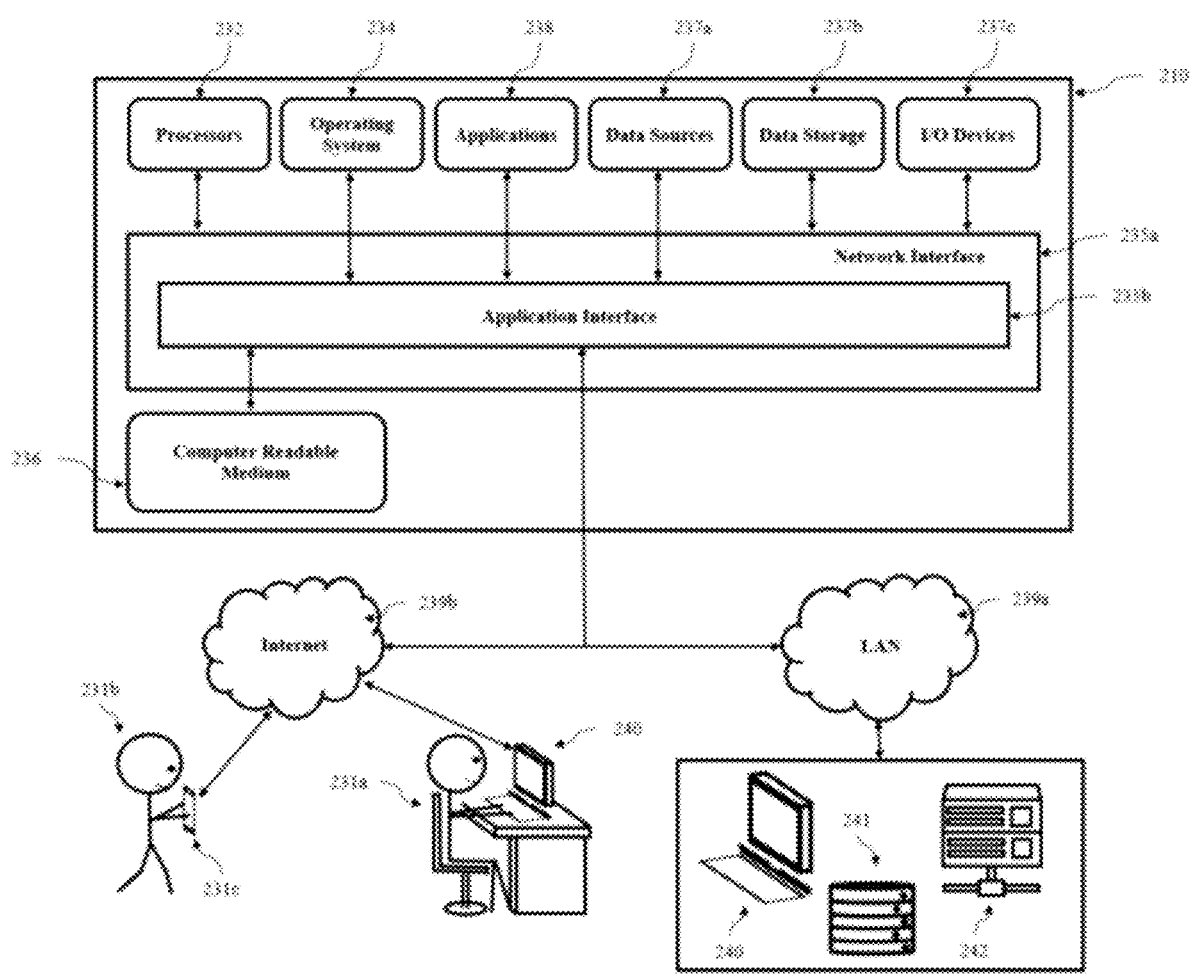
FIG. 2 illustrates a computing system enabling the systems and methods in accordance with some embodiments of the disclosure.

FIG. 2 illustrates a representative computing system 210 for enabling intelligent medical care path system 100 and associated methods in accordance with some embodiments of the system. Computing system 210, in various embodiments, can operate and/or process computer-executable code of one or more software modules of the aforementioned system and method. Further, in some embodiments, the computing system 210 can operate and/or display information within one or more graphical user interfaces (GUIs) integrated with or coupled to the system (not shown), such as a dashboard representing patient data (for either Patient or HCP use).

As shown in FIG. 2, computing system 210 can be constructed by at least one computing device including at least one processor 232. In some embodiments, the at least one processor 232 can reside in, or coupled to, one or more server platforms (not shown). In some embodiments, the system 210 can include a network interface 235a and an application interface 235b coupled to the least one processor 232 capable of processing at least one operating system 240. Further, in some embodiments, the interfaces 235a, 235b coupled to at least one processor 232 that can be configured to process one or more of the software modules (e.g., such as one or more applications 238). In some embodiments, the software modules 238 can include server-based software, and can operate to host at least one patient account and/or at least one client account, and/or transfer data between one or more of these accounts using the at least one processor 232.

With the above embodiments in mind, it should be understood that the computing system 210 can employ various computer-implemented operations involving data stored in computer systems. Moreover, the above-described databases and models described throughout can store analytical models and other data on computer-readable storage media within the system 210 and on computer-readable storage media coupled to the system 210. In addition, the above-described applications of the system can be stored on computer-readable storage media within the system 210 and on computer-readable storage media coupled to the system 210. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated. In some embodiments, of the system, the system 210 can be made of at least one computer readable medium 236 coupled to at least one data source 237a, and/or at least one data storage device 237b, and/or at least one input/output device 237c. In some embodiments, the system can be embodied as computer readable code on a computer readable medium 236. In some embodiments, the computer readable medium 236 can be any data storage device that can store data, which can thereafter be read by a computer system (such as the computing system 210). In some embodiments, the computer readable medium 236 can be any physical or material medium that can be used to tangibly store the desired information or data or instructions and which can be accessed by a computer or processor 232. In some embodiments, the computer readable medium 236 can include hard drives, network attached storage (NAS), read-only memory, random-access memory, FLASH based memory, CD-ROMs, CD-Rs, CD-RWs, DVDs, magnetic tapes, other optical and non-optical data storage devices. In some embodiments, various other forms of computer-readable media 236 can transmit or carry instructions to a computer 240, for example, and/or at least one patient 231, including a router, private or public network, or other transmission device or channel, both wired and wireless. In some embodiments, the software modules 238 can be configured to send and receive data from a database (e.g., from a computer readable medium 236 including data sources 237a and data storage 237b that can be made of a database), and data can be received by the software modules 238 from at least one other source, such as database 121.

In some embodiments of the system, the computer readable medium 236 can be distributed over a conventional computer network via the network interface 235a where the application embodied by the computer readable code can be stored and executed in a distributed fashion. For example, in some embodiments, one or more components of the system 210 can be coupled to send and/or receive data through a local area network ("LAN") 239a and/or an internet coupled network 239b (e.g., such as a wireless internet and/or Bluetooth and Radiofrequency). In some further embodiments, the networks 239a, 239b can include wide area networks ("WAN"), direct connections (e.g., through a universal serial bus port), or other forms of computer-readable media 236, or any combination thereof.

In some embodiments, components of the networks 239a, 239b can include any number of computing devices such as personal computers including for example desktop computers, and/or laptop computers, or any fixed, generally non-mobile internet appliances coupled through the LAN 239a. For example, some embodiments include personal computers 240 coupled through the LAN 239a that can be configured for any type of user. Other embodiments can include personal computers coupled through network 239b. In some further embodiments, one or more components of the system 210 can be coupled to send or receive data through an internet network (e.g., such as network 239b). For example, some embodiments include at least one patient 231 coupled wirelessly and accessing one or more software modules of the system including at least one application 238 via an input and output ("I/O") device 237c. In some other embodiments, the system 210 can enable at least one patient 231 to be coupled to access application 238 via an I/O device 237c through LAN 239a. In some embodiments, the patient 231 can be made of a patient 231a coupled to the system 210 using a desktop computer 112, and/or laptop computers (not shown), or any fixed, generally non-mobile internet appliances coupled through the internet 239b. In some further embodiments, the patient 231 can embody a mobile patient 231b coupled to the system 210. In some embodiments, the patient 231b can use any mobile computing device 231c to wireless coupled to the system 210, including, but not limited to, personal digital assistants, cellular phones, mobile phones, smart phones, pagers, digital tablets, weight scales, electro cardiograms, blood glucose monitors, and/or fixed and/or mobile internet appliances, etc.

Any of the operations described herein that form part of the computing system are useful machine operations. The computing system also relates to devices or apparatus for performing these operations. The apparatuses can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general-purpose computer selectively activated or configured by one or more computer programs stored in the computer memory, cache, or obtained over a network. When data is obtained over a network the data can be processed by other computers on the network, e.g. a cloud of computing resources.

The embodiments of the computing system 210 can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally, or in particular formats that enable the construction or depiction of a physical and tangible object. In some embodiments, the manipulation can be performed by a processor. In such an example, the processor thus transforms the data from one thing to another. Still further, some embodiments include methods which can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

While HCPs are often skilled medical professionals who receive constant training and updates to the latest medical procedures, not all HCPs use the same approaches to diagnose and treat patients. Lack of standardization in diagnosis prescriptions, treatment, and management can be attributable to variations in training, participation, and willingness of HCPs to adopt different approaches. Further, even when using similar approaches, many techniques for diagnosing ailments, determining when to initiate treatment, determining which treatment to provide, how aggressively to treat the ailment, and similar considerations are often based on subjective criteria, thus leading to a further lack of standardization and objectivity amongst HCPs. As a result, patients can be less inclined to trust a diagnosis or care path prescribed by HCPs and thus fail to fully engage in the prescribed care path to the detriment of the patient's health. Further, HCPs can falsely believe or perhaps be unsure whether they will be reimbursed by insurers/government programs for certain treatments and thus either take a loss or stray from recommending a particular treatment for fear of not being reimbursed. One of ordinary skill in the art can recognize additional negative implications of a lack of standardization and objectivity in diagnosis and treatment approaches amongst HCPs within the scope of the present disclosure.

Systems and methods of the present disclosure, in at least one aspect, can be configured to advantageously address these implications by promoting personalization, standardization and/or objectivity amongst HCPs throughout the diagnosis and treatment processes. In particular, intelligent medical care path system 100 and methods associated therewith can use a combination of big data, machine learning, and/or regression equations to make living care paths based on sensitivities, probability, and/or statistics, which increases the chances of a care path being successful. The living care path system 100, in some embodiments, can also provide a visual representation of the treatment options and statistics to the patient and HCP. As configured, intelligent medical care path system 100 can empower patients, making them more informed about their condition, expectations of recovery, and more confident in their HCP's recommended treatment measure.

The system is uniquely tailored to collect the data from the patient to use in the statistical analysis. From the time prior to initial contact with the HCP, to when the patient is directed to use the intelligent medical care path system 100, the intelligent medical care path system 100 is collecting information. The patient 231 can enter information manually through the use of a computer 112 or mobile application on a mobile device in the waiting room of a health care facility 292, for example, but information can also be gathered by wearable mobile devices such as a phone or tablet 110 or a smartwatch 111, where the mobile devices have sensors and components managed by programs and/or applications that deliver health data (e.g. biometric, physiologic, co-morbidities, etc.) to the system 100. In the case of manual entry, the system can support the living care path by prompting a patient 231 to enter information about themselves and/or their state of health at a predetermined frequency. Because of the constant analytics the system 100 performs on the data collected, the frequency of data collection can be adjusted throughout treatment. This adjustment improves the efficiency of the treatment measure (e.g. by decreasing collection entry frequency after a clear improvement trend or increasing frequency if the system 100 detects a significant problem). In the case where a patient 231 does not have access to a computer, they can contact an HCP 291 who can also enter a patient's data using a computing device 113. The HCP 291 can also accesses the system 100 using computing device 113 to check patient health data (e.g. biometric, physiologic, co-morbidities, etc.) at any time, as well as review administrative items, such as reimbursements submitted and/or received for items relating to a patient's living care path, patients' use of or engagement with intelligent medical care path system 100.

The intelligent medical care path system 100, in various embodiments, is also uniquely configured to collect and aggregate all patient 231 information and provide a robust data pool for analysis of factors that contribute to optimal diagnosis, prescription, treatment, and management of a given patient based on what worked for similarly or most similarly situated patients and/or diseases. In various embodiments, the intelligent medical care path system 100 uses one or more of artificial intelligence (AI), machine learning, random forest, linear regression, a recurrent neural network (RNN), etc. to aggregate and/or analyze data. The intelligent medical care path system 100 can use any current or historical patient data when performing the analysis. In various embodiments, the system uses outside sources such as a database 121 that has historical data sets such as articles and/or research relating to a patient's symptoms to supplement the analysis or manually entered care paths by HCP's. The aggregated information is then linked by the intelligent medical care path system 100 to a particular diagnosis, set of symptoms, and/or living care path, and the successes and failures associated with those parameters becomes the data pool for analysis relating to optimal diagnosis and treatment for the next patient. In this way, the system "learns" what treatment measure or set of actions to suggest for future patients for a given set of conditions. The intelligent medical care path system 100 goes beyond the analysis an HCP can provide even when the HCP has access to the same information, as it can correlate trends in data such as, but not limited to, sleeping habits, time of day, severity of symptoms, age, race, genetic predisposition, prior illnesses/ailments, geographic location, weather impact, longitudinal diet, and/or symptom location. In various embodiments the trends are correlated against historical trends to identify potential root causes that cannot be evident from a cursory or deep review of information. This helps HCP's avoid delayed, wrong, or missed diagnoses. For example, an HCP that does not use the intelligent medical care path system 100 to monitor a patient can misdiagnose a heart attack as acid indigestion based on reported symptoms in a brief examination. However, using various embodiments of the system, a patient in a waiting room can be asked to attach certain medical devices for monitoring heartrate and blood pressure, for example. At the same time, a dynamic set of questions can be asked by intelligent medical care path system 100, such as eating habits, heartburn frequency, and/or any other relevant information. Each question answered leads the system to another relevant question and is analyzed in conjunction with the patient's health data (e.g. biometric, physiologic, co-morbidities, etc.), until the system converges on a probable diagnosis. This collected information could be used to inform the HCP that there is a much higher probability of a heart attack than acid indigestion, and even alert medical staff that the patient needs immediate attention. This can be a lifesaving feature in the reverse case as well, where the patient makes an appointment for what they believe is severe acid indigestion, but is told by the system 100 to report immediately to an emergency room at a health care facility 292. In some embodiments the system 100 performs one or more of alerting a HCP 291 of the incoming patient, pre-populates reimbursement forms, reschedules the HCP's appoints for the day, recommends a treatment measure, and/or gives an estimate for when the patient will reach some critical threshold. In some embodiments, the intelligent medical care path system 100 provides a checklist for medical procedures and/or even surgery based on the newest and most advanced techniques gathered from various databases 121, further regaining lifesaving seconds and providing the patient and HCP with the highest probability of success.

Figure 3A:
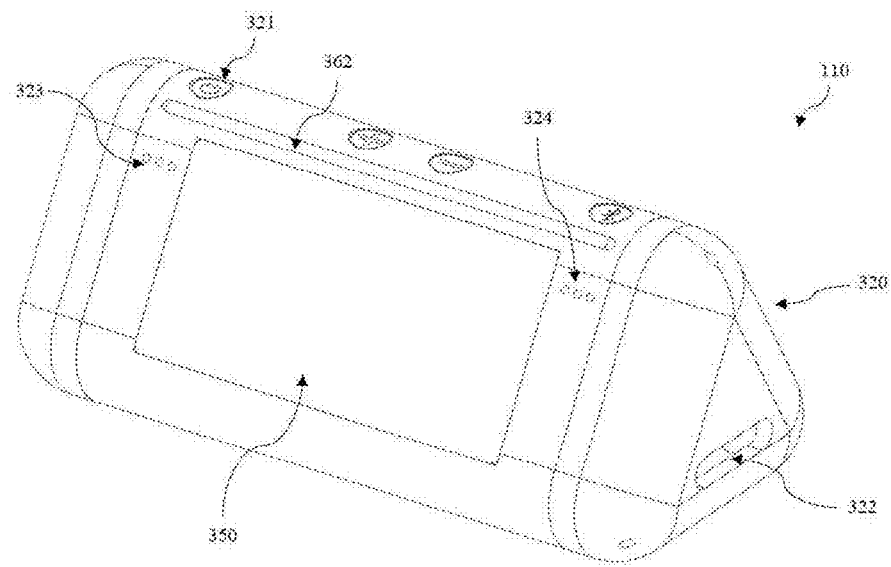
FIGS. 3A and 3B are isometric views, both assembled and exploded, of an embodiment of a patient hub apparatus.
Figure 3B:
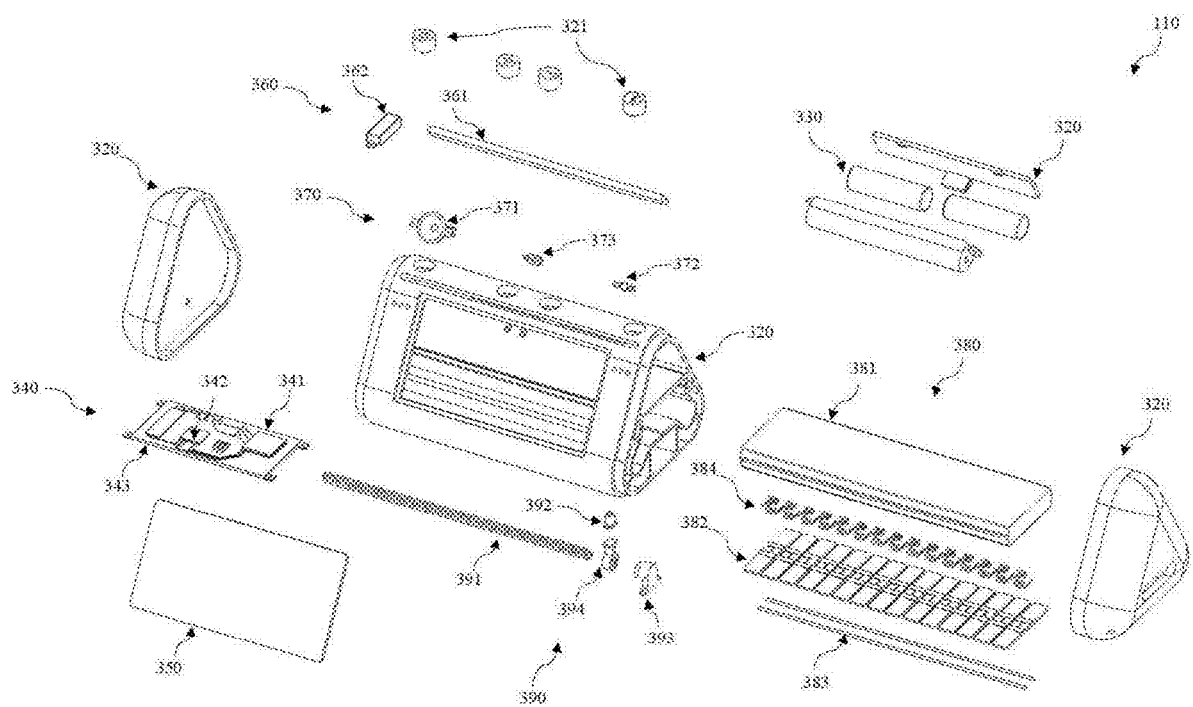

Now referring to FIGS. 3A and 3B, an embodiment of the computing devices and systems 110 and/or 210 is shown. In one embodiment, the computing devices and systems 110 and/or 210 are a patient hub apparatus. The patient hub apparatus 110 and/or 210 is a patient engagement device embodiment that directly or indirectly collects a plurality of medical data. This medical data is collected from a variety of sources, for example: a preclinical survey, electronic medical records, data from the internet or other, connected databases, and monitoring devices from computing devices 110, 111, 112, 113, 231c, and 240. These inputs are aggregated in various data sets. One data set can include clinical data such as: biometrics exemplified by gender, age, etc. Another data set can include family history such as: prior disease, age of death, and geography of home, etc. Another data set can include disease state evaluation such as: Kellgren & Lawrence classification of "grades" or "severities" of osteoarthritis "K&L", stages of a cancerous tumor, stage of RA (rheumatoid arthritis) progression namely CDAI—Clinical Disease Activity Index and/or RAPID-3, etc. Another data set can include interventions such as: physical therapy, pharmacy, surgery, etc. Another data set can include physiological data such as: weight, heart rate, respiration rate, etc. Another data set can include non-physiological biomarkers such as: muscle strength, steps, range of motion of limb, etc. Another data set can include survey data such as: patient-reported outcomes "PRO", patient-reported function and performance, pain level, etc. Another data set can include device specifics such as: urinalysis, blood pressure, sleep cycle, etc. Another data set can include personal inputs such as: goals, patient availability, occupation, marital status, etc. Another data set can include environmental inputs such as: air quality, weather near residence, etc. This data can be stored in the cloud, a physical network, or a local device.

A patient hub apparatus 110 and/or 210 is made of a housing 320 containing electronic circuitry 340 including a processor 341 operably coupled to a memory, electronic connectivity and a power source 330, wherein the memory stores computer executable instructions and a processor that executes the instructions to cause the patient hub apparatus 110 and/or 210 to perform various functions. These functions can include telehealth enablement by virtue of audio and video capacity. These functions can also include a graphical user interface for presenting data such as a red/yellow/green color illuminator showing progress of living care path, action needed toward living care path, survey inputs or results, etc. These functions can also include an alert system 360 including lights 361 and a haptic vibrating motor 362 for indication to a user that some action may be needed.

These functions may also include a pill dispenser and tracker of use by providing physical storage for prescriptions, over the counter medication, nutritional supplements, etc. These functions may also include cellular enablement for all data transfer to and from the patient hub apparatus 110 and/or 210 to databases (cloud, physical, etc.) 121 for the purposes of access by any potential users such as the HCP, patient, etc. 231 and 291. These functions may also include the capacity to bridge and provide needed database 121 connectivity through other connected devices using a cell signal, wifi, Bluetooth, etc. These functions may also include connectivity to data entry devices such as a watch, weight scale, blood pressure cuff, pedometer, etc. These functions may also include direct entry via a touchscreen display 350, connected-device, physical button 321, etc. These functions may also include the capacity to receive contextual or environmental information about the patient such as internet weather for the day, news, or personal systems such as home generator, local utilities, email volume, phone usage, etc. The patient hub apparatus 110 and/or 210 includes a hard drive to record data.

Figure 9:
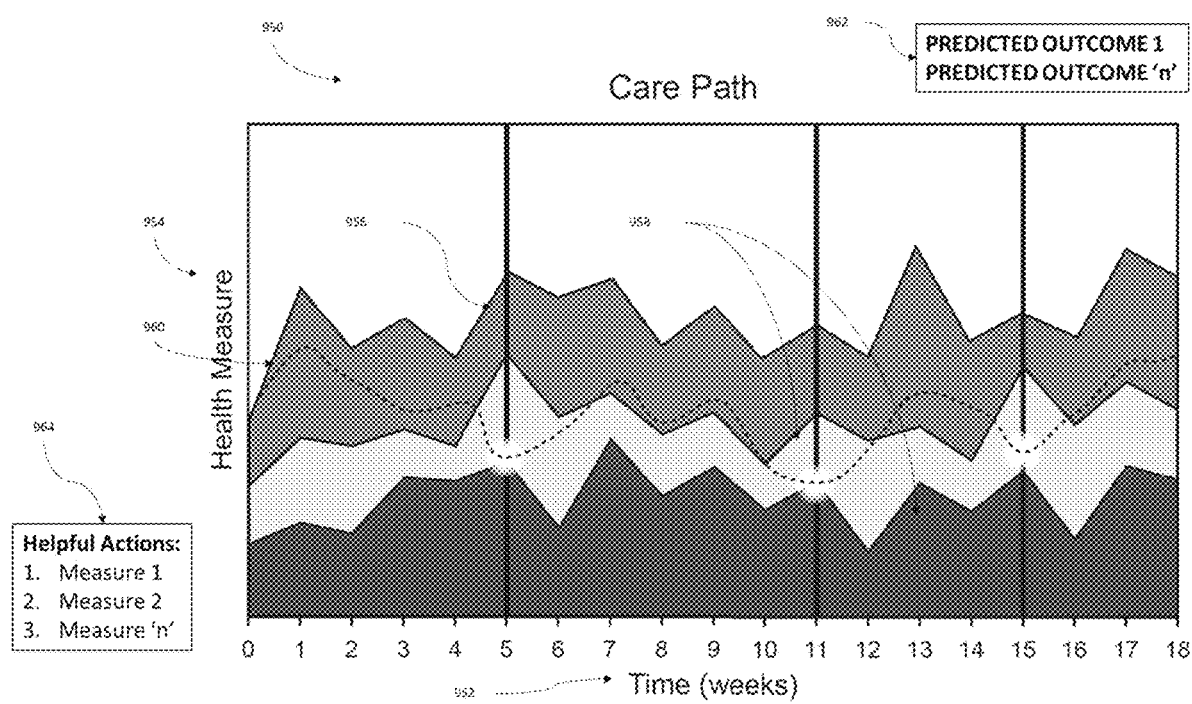
FIG. 9 is an illustration of a living care path graphical user interface.

Now referring to FIG. 3A, an embodiment of the computing devices and systems 110 and/or 210 is shown. In one embodiment, the computing devices and systems 110 and/or 210 are a patient hub apparatus. The embodiment of the patient hub apparatus 110 and/or 210 shown is made of various components, one of which is a housing 320. This housing 320 can be made of one or multiple pieces as shown in FIG. 3B. The housing 320 can be made of a rigid material such as plastic or aluminum. The housing 320 can include a display screen 350. The display screen 350 can be a direct method of medical data capture. It also can display the living care path as a graphical user interface as shown in FIG. 9. As shown in FIG. 3B, the embodiment of the patient hub apparatus 110 and/or 210 shown is made of: housing 320, display 350, power source 330, electronic circuitry 340 which includes: processor 341, memory, cellular connectivity chip 342, and Bluetooth connectivity chip 343. The patient hub apparatus 110 and/or 210 also has telehealth capability 370 which includes: speaker 371, microphone 372 and camera 373. A data input device such as a display 350 can include the buttons 321 and a connected device 110, 111, 112, and/or 210.

Now referring to FIG. 3B, the patient hub apparatus 110 and/or 210 has a medicine storage apparatus 380. The medicine storage apparatus 380 shows an example of an embodiment made of: the medicine storage housing 381, the medicine storage housing doors 382, the medicine storage housing pins 383, and the torsion springs 384. The patient hub apparatus 110 and/or 210 has a medicine dispensing apparatus 390. The medicine dispensing apparatus 390 shows an example of an embodiment made of: a threaded rod 391, a linear actuator motor 392, a rotation motor 393, and a coupler having internal threads 394. The linear actuator motor 392 is attached to the coupler having internal threads 394 which translates along a threaded rod 391 by action of the rotation motor 393. The linear actuator motor 392 has a rod that pushes on the medicine storage housing door 382 which dispenses the stored medicine.

Figure 4:
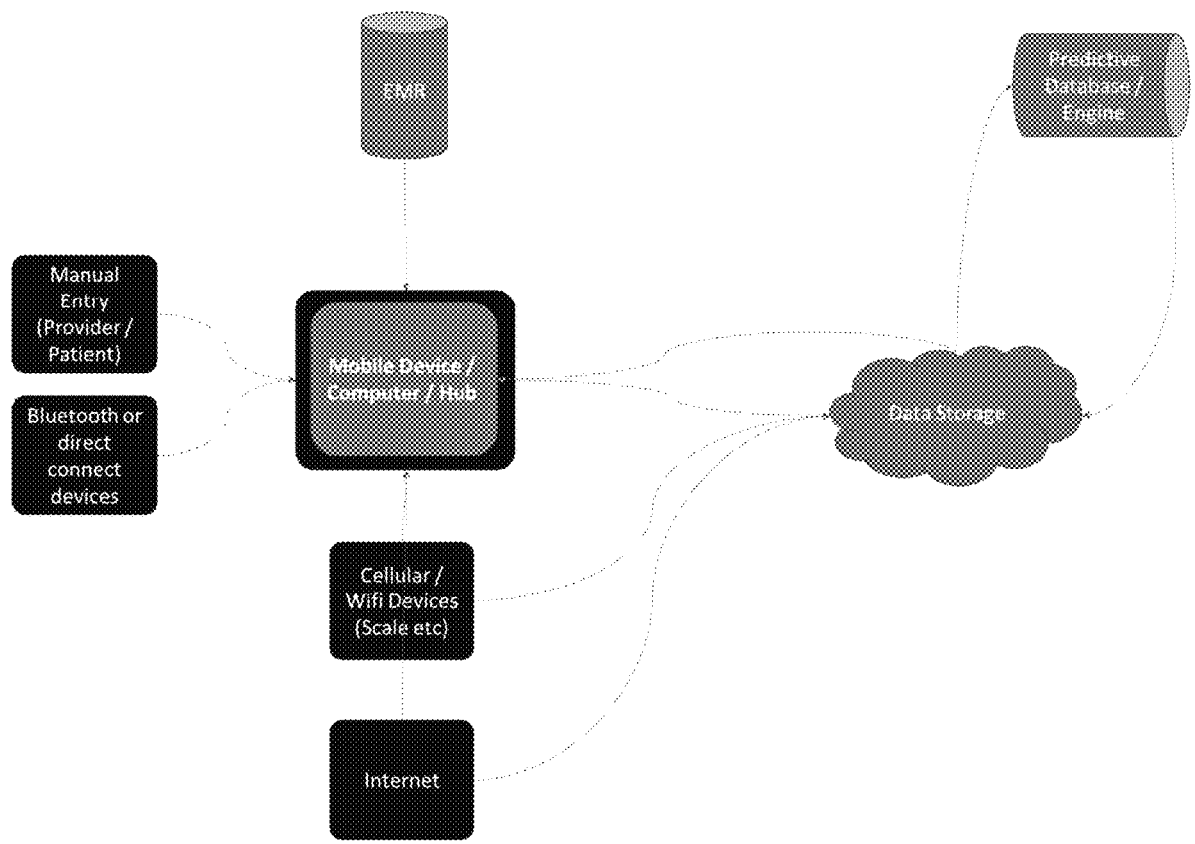
FIG. 4 illustrates a computing system for the computing device for electronic communication.

Now referring to FIG. 4, a computing system 210 is shown. The computing device 110 is in electronic communication with one or more devices such as medical devices. These medical devices can include: a blood glucose meter; a pacemaker, a blood pressure monitor; an insulin pump, a pulse oximeter, an electrocardiograph, an electroencephalograph, a blood alcohol monitor, an alcohol breathalyzer, an alcohol ignition interlock, a respiration monitor, an accelerometer, a skin galvanometer, a thermometer, a patient geolocation device, a weight scale, an intravenous flow regulator, a patient height measuring device, a biochip assay device, a monitor for biological agents, a hazardous chemical agent monitor, an ionizing radiation sensor, a sphygmomanometer, a loop recorder, a spirometer, an event monitor, a prothrombin time (PT) meter, an international normalized ratio (INR) meter, a tremor sensor, a defibrillator, a urinalysis device, a pulse oximeter, a dynamometer, etc. The computing system 210 can receive medical data from EMR (history biometrics, PROs, treatment etc.) and/or manual entry from the provider or the patient (history biometrics, PROs, treatment, environmental (SDH), etc.). The computing system 210 can receive medical data from direct connect device or BLUETOOTH devices (physiologic and non-physiologic data). The computing system 210 can receive medical data from cellular WIFI devices (physiologic and non-physiologic data). The computing system 210 can receive medical data from the internet (weather, social status, etc.). The data can be transmitted to data storage and to a predictive database/engine.

While not shown, in some embodiments, the various components of living care path system 100 could instead be provided on a single device used by patient 231, rather than via a distributed system architecture, as previously noted. As configured, all data can be stored, processed, and analyzed locally on the device, including generating associated feedback and recommendations locally on the device. Such an approach can be favorable from the standpoint of promoting compliance with privacy laws, such as HIPPA, since the data would remain on the device within the possession, custody, and control of the patient rather than transmitting the data over a network, where it could potentially be intercepted or accessed by an unauthorized person.

Figure 5:
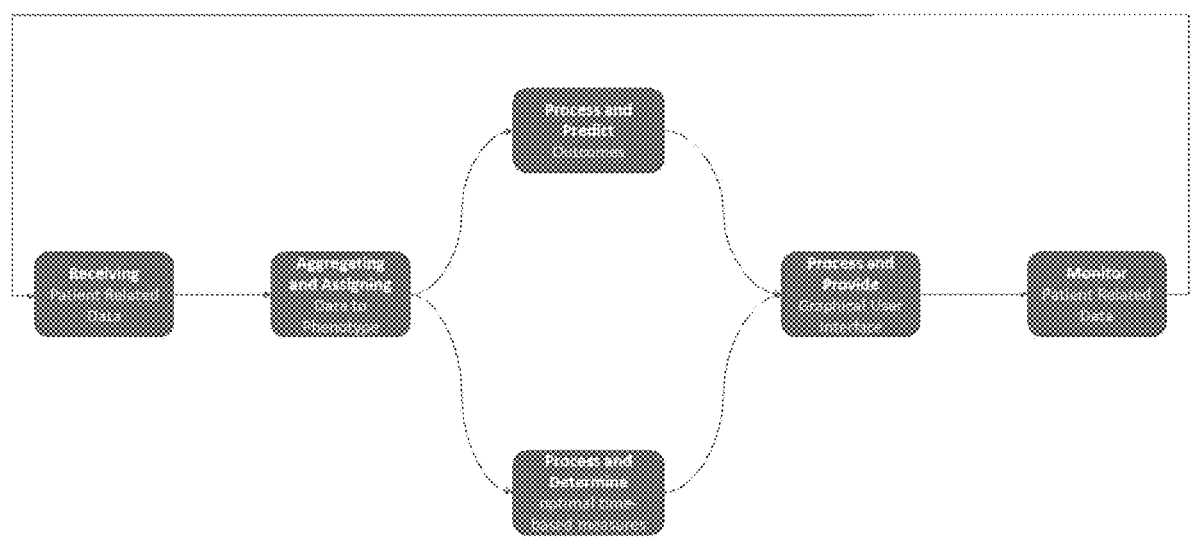
FIG. 5 illustrates the method and system of the living intelligent care path.
Figure 6A:
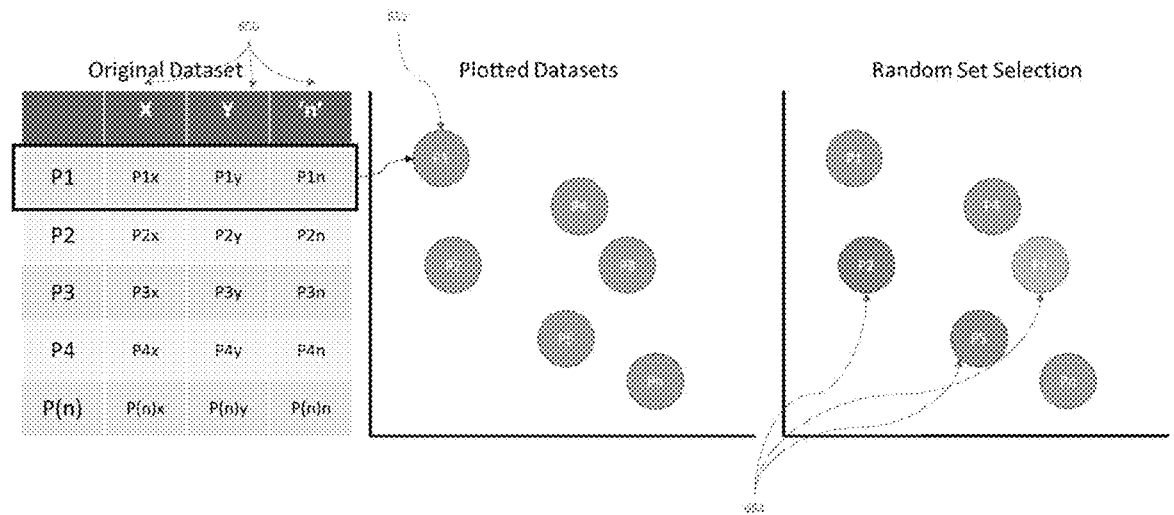
FIG. 6A and FIG. 6B are illustrations of a machine learning process according to an embodiment of the present disclosure showing clustering into phenotypic groups.
Figure 6B:
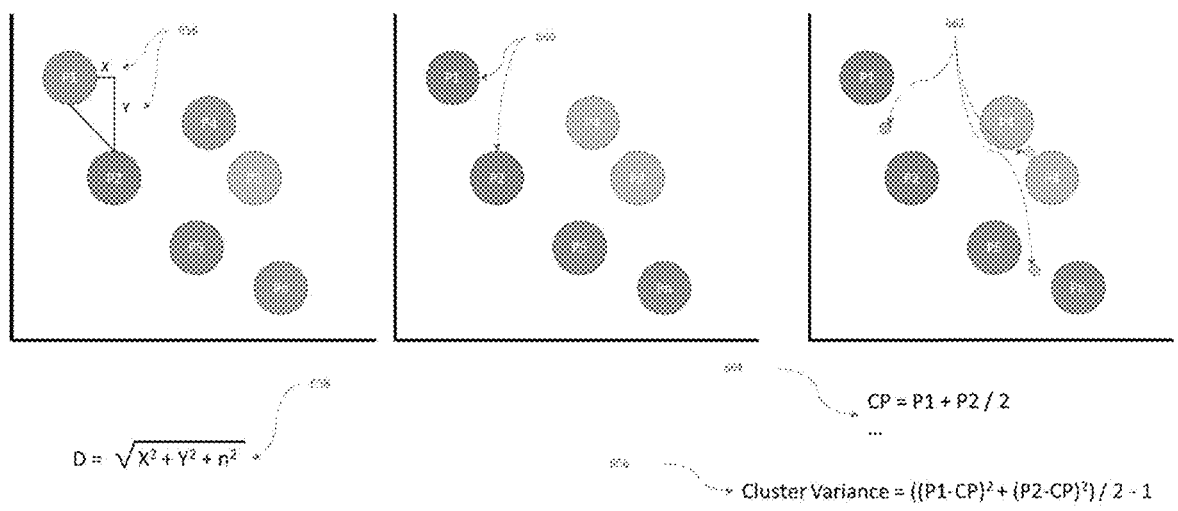
Figure 7A:
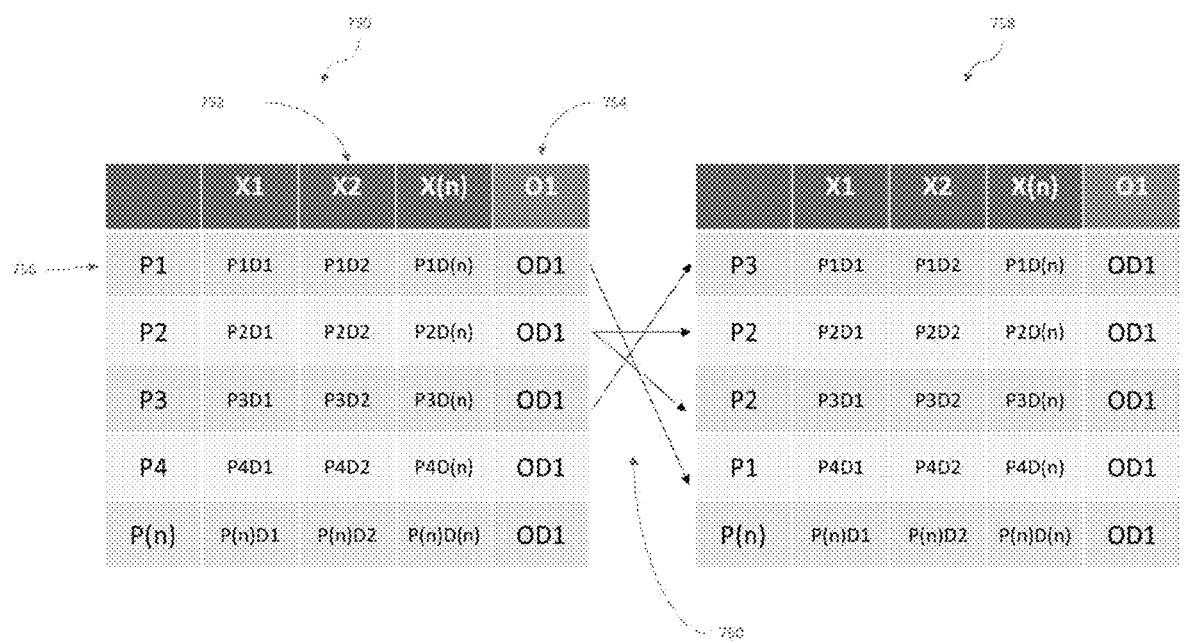
FIG. 7A-7E are illustrations of a machine learning process according to an embodiment of the present disclosure showing a random forest outcome prediction.
Figure 7B:
Figure 7C:
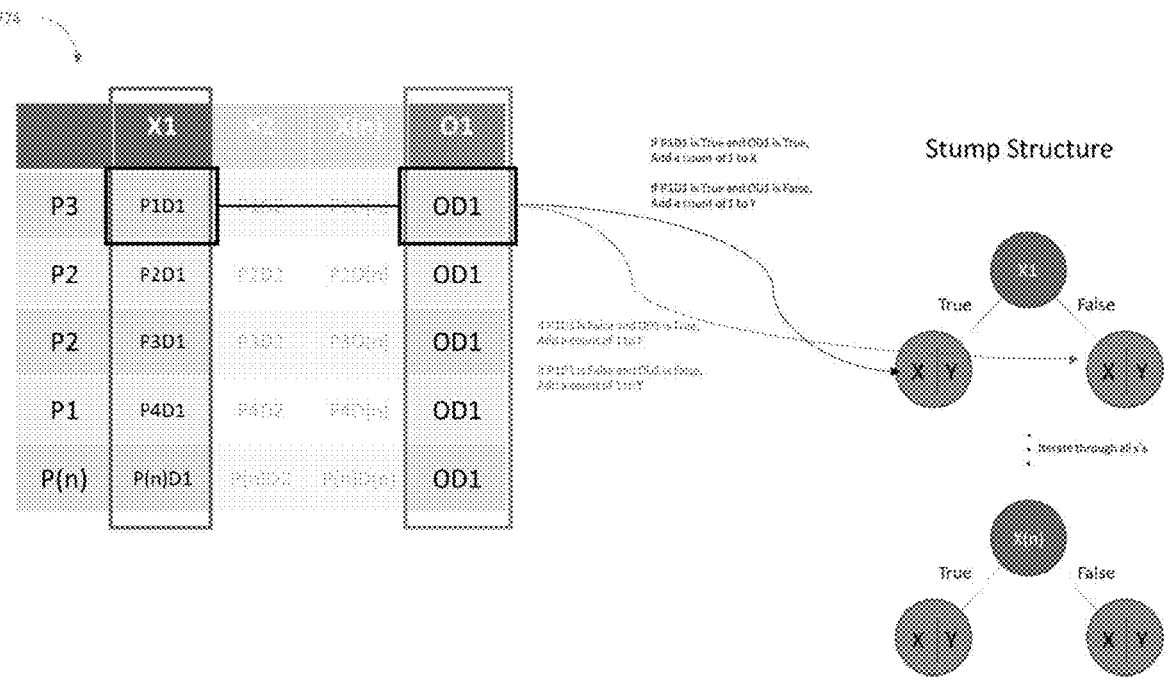
Figure 7D:
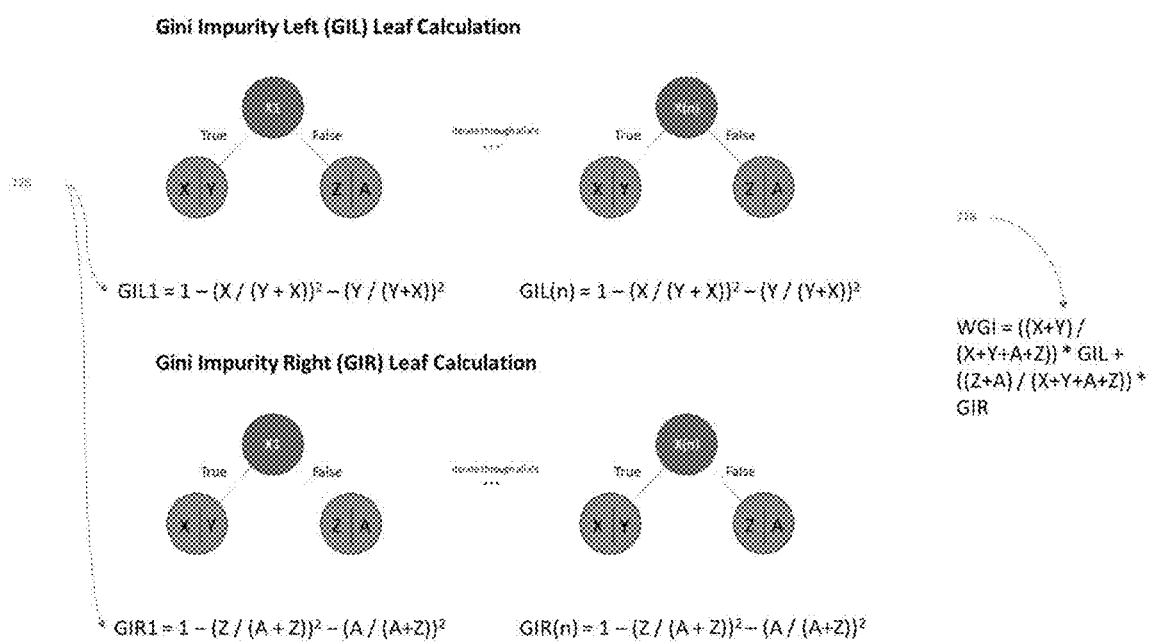
Figure 7E:
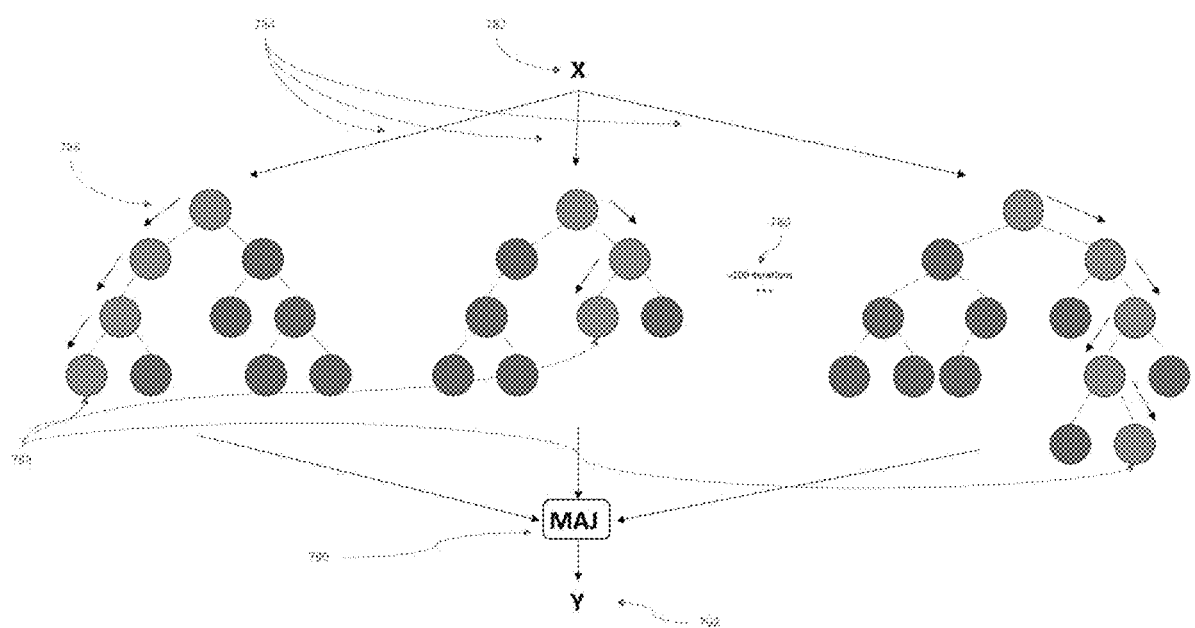
Figure 8:
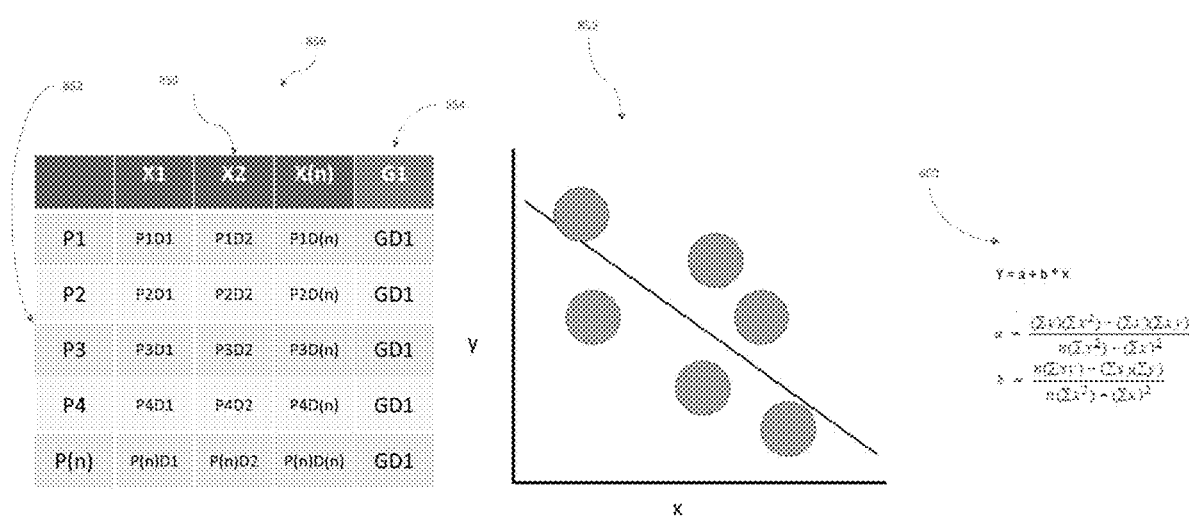
FIG. 8 is an illustration of a machine learning process according to an embodiment of the present disclosure showing a regression to predict time-based, goal-sensitive measures.

Now referring to FIG. 5 an intelligent living care path method is shown. This method includes a non-transitory computer-readable medium storing instruction that, when executed on a computing device, cause the computing device to perform a method for providing a patient's living care path. The method includes the step of receiving patient related data from one or more data sources. These sources can include one or more computing devices such as: a mobile device or tablet 110, wearable device 111, a patient hub apparatus 110 and/or 210, or desktop or laptop computer 112. The next step of the method includes aggregating a plurality of medical data sets from one or more data sources into one or more phenotypic groups to assign at least one phenotypic group.

Subsequent steps in the method can occur sequentially or simultaneously and are only numbered to differentiate the steps. One step includes first processing the plurality of medical data sets of at least one assigned phenotypic group to predict one or more patient outcomes and another step includes processing the plurality of medical data sets of the assigned phenotypic group to determine an optimal time based set of measures for increasing the probability of attaining at least one living care path goal. The one or more patient outcomes and the optimal time-based set of measures are processed by the computing system to provide the living care path graphical user interface, as shown in FIG. 9. FIG. 9 is an illustration of a graphical user interface showing the living care path. FIG. 9 shows the differential between the living care path and present performance and a plurality of measures to alter this differential.

Now referring to FIGS. 5-8 an intelligent living care path method and system is shown. This method includes a non-transitory computer-readable medium storing instructions that, when executed on a computing device, cause the computing device to perform a method for providing a patient's living care path. The method includes the step of receiving patient related data from one or more data sources. These sources can include: one or more computing devices such as a mobile device or tablet 110, wearable device 111, or desktop or laptop computer 112. The next step of the method includes: aggregating a plurality of medical data sets from one or more data sources into one or more phenotypic groups to assign at least one phenotypic group. In some embodiments, historical data sets from the computing system 210 and/or databases 121 linked to computing system 210 as described above are provided as input factors. In this embodiment, the term aggregation means the clustering of data sets into phenotypic groups and assignment of one or more phenotypic groups, such as, but not exclusive to k-means clustering. As an example of how to achieve this, first gather the all of the data inputs per patient (650). Second, factor out any outlier data inputs which all patients do not have. Third, determine the best 'k' by running the clustering algorithm and determining the mathematical elbow point plotted by beginning with k=1 and enumerated through k='n' where 'n' generates a variation of 0 because it is equal to the total number of data inputs available, and with this output, select the elbow point, which is the inflection point of maximum reduction in variance, and assign it as 'k'. Fourth, leveraging this 'k', iteratively run the clustering algorithm by plotting the data sets by patient (662), randomly selecting 'k' number of points and define each as a unique cluster (664), measure distances between all points relative to the selected cluster points leveraging Euclidian distances (656 and 658), classify each point into its nearest clustered phenotypic group (680), when all points are classified into a phenotypic group, calculate each clustered phenotypic group's centroid through mean measurement (662 and 664), then calculate the variation within each cluster from its centroid (686) and document this variation. Fifth, repeat the phenotypic clustering from steps three through 4 for a 'k' number of times. Sixth, select the clustered phenotype iteration which has the minimal amount of variation within each clustered phenotype group overall. Seventh, note the assigned clustered phenotype group that the patient related data set has been assigned for further processing of prediction of both outcome and sensitive measures effecting goal(s). See Knoop J, van der Leeden M, Thorstensson C A, Roorda L D, Lems W F, Knol D L, Steultjens M P M, Dekker J. Identification of phenotypes with different clinical outcomes in knee osteoarthritis: data from the osteoarthritis initiative. Arthritis Care Res. 2011; 63:1535-42. as a reference of use for this example of methodology in practice.

The next step of the method includes: processing the plurality of medical data set of the at least one assigned phenotypic group to predict one or more patient outcomes (which can be run in sequence or parallel with 00047). In some embodiments the prediction is achieved by leveraging one or more machine-learning or deep-learning operations, such as, but not exclusive to, random forest, dynamic Bayesian network, multi-linear regression algorithm, recurrent neural network methods. Other methods of performing similar types of operations may be performed within the scope of this disclosure as will be apparent to those of ordinary skill in the art. In some embodiments, historical data sets from the computing system 210 and/or databases 121 linked to computing system 210 as described above are provided as input factors in a deep-learning operation. An example of this would be a random forest operation. To accomplish this, first plot all the data inputs per patient within their phenotypic group into tables based on the total number of respective outcome possibilities (750). This will include individual patient data category(ies) (752), individual patient outcome(s) (754), and the respective individual patient datasets (756). Second, for each respective phenotypic group outcome data table plot (750), create a bootstrapped data table plot (758) by randomly selecting patient data groups and forming a new data table plot which can and should include redundant entries of data inputs from the same patient (760) and then execute a decision tree creation from each of these bootstrapped data tables (762). The decision tree made of at least one Root Node (764), one branch (766), one internal node (768), and one leaf node (770). Leveraging only both a randomly selected number of and specific type of data input categories at each node creation step (from root to end) by first determining root node through creation of stump nodes (772) and subsequently calculating how well every individual patient data category (752) predicts the individual patient outcome (754) by selecting the measure with the lowest gini impurity for each leaf node (774). To accomplish this, subtract 1 from the probability of successful goal prediction squared and subtracting again the probably of unsuccessful goal prediction squared for both leaf nodes within the stump (776) and then determine the gini impurity for the overall node through a weighted average calculation of gini impurities for both leaf nodes and select the root node by determining which has the lowest overall gini impurity for all possible selection (778), and then with this root node assigned, leverage its stump node, gather only the patient data input categories from patients within the left leaf node and determine their gini impurity only (as described above), and select the lowest gini impurity input as the next node and then repeat these calculations until all left nodes terminate with 2 leaf nodes or until the score itself has a lower gini impurity score than its higher node and then it becomes a leaf node, and then subsequently execute these same factors for the right node of the second level node stump and enumerate all nodes from left to right until termination and completion of a decision tree (762). Third, repeat the first two steps more than one-hundred times thereby creating at least one-hundred varying decision trees from varying bootstrapped datasets and randomly selected data input categories for each node created within each decision tree (780). Fourth, plot the patient data that was not sampled during the random selection for bootstrap creation into a data table and execute the random forest with each patients' data from this excluded data table until complete and tabulate, within the random forest of multiple decision trees, each decision tree's error rate (the higher the number of incorrect outcomes the higher the error). Fifth, an acceptable error rate may be selected by a user such as an HCP or patient and exclude any decision trees below this level. Sixth, calculate the selected patient data set (782) with the selected random forest's decision trees to predict the most likely set of outcomes by inputting into the various, created decision trees concurrently and independently (784), allowing each tree to determine its own decision tree path (786) and resulting in each decision tree's own output (788). Then, sum all of the outputs (790) and select the majority output as the final output to the operation (792). See Rahman, R., Matlock, K., Ghosh, S. & Pal, R. Heterogeneity aware random forest for drug sensitivity prediction. Sci. Rep. 7, 11347 (2017). as a reference of use for this example of methodology in practice.

The next step of the method includes: processing the plurality of medical data set of the assigned phenotypic group to determine an optimal time based set of measures for increasing the probability of attaining an at least one living care path time-based measure which will affect the goal(s) (which can be run in sequence or parallel with 00046). In this invention the optimal time-based set of measures are determined by leveraging one or more mathematical models for applied statistics, such as, but not exclusive to, design of experiments (DOE), symbolic regression, or multiple linear regression. An example of this would be multiple linear regression. To accomplish this, first plot all the data inputs (850) per patient (852) within their phenotypic group into tables based on the total number of respective goals (854)—a table being created for each goal (856). Second, determine the best fit line within the data set (858) by determining both the slope and y-intercept of that line through the execution of a linear regression equation (860) for each data set plotted. Third, an acceptable correlation coefficient may be selected by a user such as an HCP or patient and exclude any outputs falling below this threshold as not having a meaningful impact on the respective goal selected. Finally, select the outputs above the set threshold as the output(s) of the operation. See Schneider A, Hommel G, Blettner M. Linear regression analysis: part 14 of a series on evaluation of scientific publications. Dtsch Arztebl Int. 2010; 107(44):776 as a reference of use for this example of methodology in practice.

The next step of the method includes: processing said one or more patient outcomes and said optimal time based set of measures for providing the living care path embodied as a graphical user interface showing said outputs from earlier operations, such as, but not exclusive to: i) the differential between the living care path and present performance of the patient ii) a plurality of measures to alter this differential iii) at least one predicted outcome (950). In this embodiment a living care path is the combined outputs of the predicted patient outcome, the time-based measures affecting goal(s), and at least one longitudinal series of goals-based set of thresholds for purposes of tracking patient performance relative to them. In this embodiment the living care path graphical user interface may be presented via numerous devices, such as a mobile device. It would give visual indication of all output operations to provide a time based (952) and health measure (954) specific set of longitudinal goals or thresholds (956), along with thresholds of at least two levels of concerning performance (958), the patient's tracking towards those thresholds (960), the listing of the predicted outcome(s) (962), and a listing of measures which will most probably impact the patient's tracking toward goals or thresholds (964), allowing both HCP and patient to visually track progress toward living care path and gauge manual intervention to support. Alternatively, intervention thresholds may be set by either a time interval or a performance level which will execute the patient's data inputs to be re-evaluated through these above methods—thereby re-organizing the living care path's graphical user interface visualization and allowing a newer set of parameters to be assessed for action which will ultimate optimize the health measure's probability of attainment.

In various embodiments, the random forest provides the following advantages over the prior art: aggregation of large amounts of data to improve statistical confidence of health care paths; patient specific health care paths that provide personalized optimization and improved outcomes; evidence based health care path protocols; higher patient satisfaction levels; scaling of improved outcomes; and ability to automate successful health care path techniques and prequalification from the best of best.

In various aspects of the system, big data and analytics are used to assist an HCP when diagnosing a patient's symptoms and providing an optimized patient health care path. The big data and analytics play a crucial role in this process, as data entry for area of and/or frequency of symptoms into the system can link a specialized HCP to a broader class of probable causes and/or treatment solutions. Success, or failure, of treatments relating to an HCP diagnosis are then fed back into the system through data collected over the execution of the living care path. This improves future diagnosis as the system dashboard can display statistical analysis such as probability percentage for each of a range of possible conditions that match a particular set of symptoms, for example. These early diagnostic probability percentages can change during the course of treatment. If so, the system alerts the HCP that a new diagnosis and/or treatment measure can be required and provides analytics for support and conversely the system can reward or commend a patient for successfully managing against risks.

Big data and analytics are continuously performed on the patient related data (e.g. biometric, physiologic, co-morbidities, etc.) collected by the system while a patient is on a health care path in some embodiments. The system allows an HCP to monitor numerous patients at the same time without physically having to check-in with them to get a description of their current condition. In this respect, the system itself acts as an HCP as it is configured to continuously monitor the patient and use big data and analytics to diagnose the root cause of even the smallest change in a patient's data. An example where this can be a lifesaving feature is in the case where the patient doesn't even know there is a change, such as in the case of increased blood pressure or a change in chemical levels in the blood stream. A fluctuation in these types of parameters can be an indication that the patient should immediately seek medical attention. Combining fluctuations in these types of parameters with the time of the day, for example, can provide valuable insight to outside influences affecting a patient's health. The system can have all of this information available to the patient and/or HCP as soon as they open their dashboard.

FIG. 1 is a flowchart depicting a method of using the medical system 100 to facilitated health care monitoring, analytics, and planning according to an embodiment of the present disclosure. Viewed in combination, FIG. 1, FIG. 2, and FIG. 4 illustrate medical system 100 as used by a patient and an HCP 291 in an exemplary medical treatment process. As shown, medical system 100 can be configured to evaluate information provided by a patient 231 to assess the medical condition of a patient and ultimately suggest a HCP to the patient, and/or provide a HCP 291 with sufficient data and information to make a medical diagnosis and prescribe a treatment measure or make the diagnosis and prescription with or without associated statistics itself.

In further reference to the exemplary embodiment of FIG. 1, FIG. 2, and FIG. 4, the method starts with patient 231 downloading one or more medical system applications 238. In some embodiments the application 238 present as a dashboard which is not shown but discussed in further details below. In some embodiments the application 238 is configured to notify the patient to updates, alerts, or other information that the computing system 210 generates. In some embodiments the notification is displayed on the dashboard.

Figure 10:
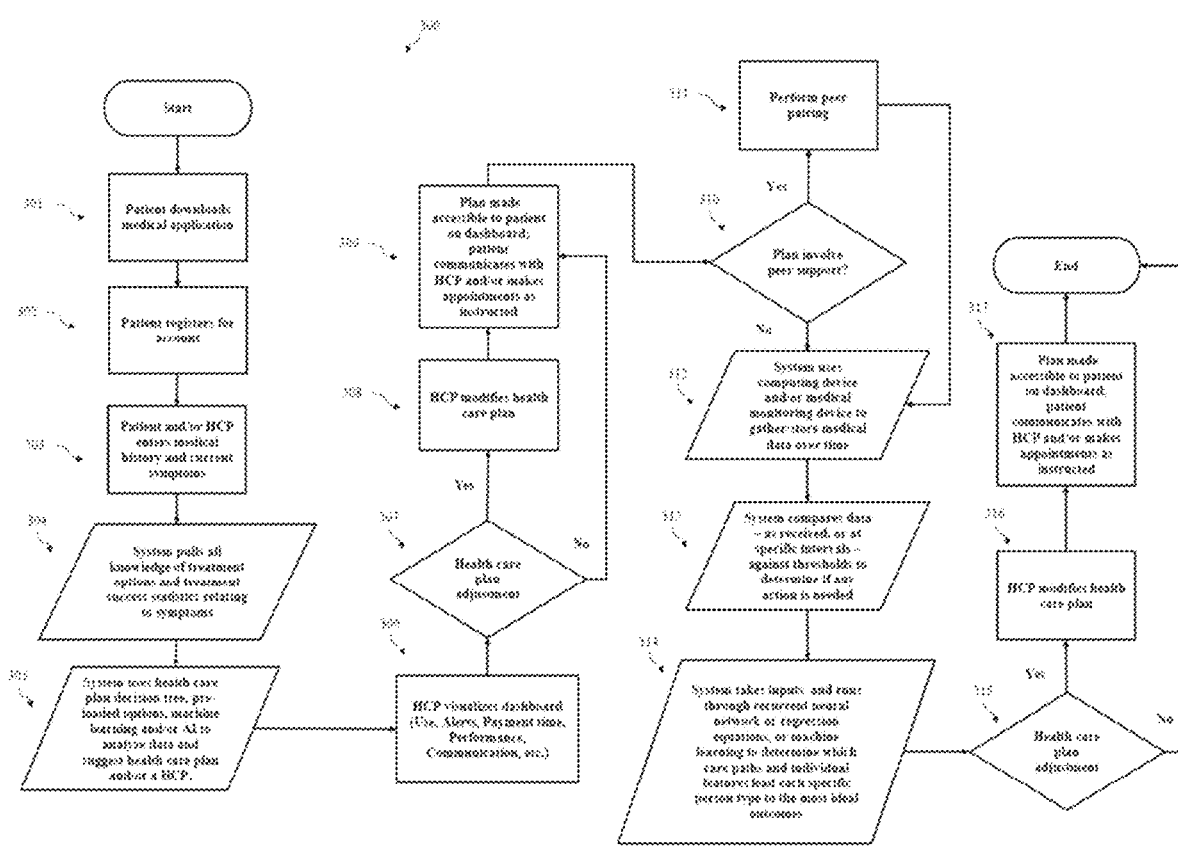
FIG. 10 is a flowchart depicting a method for facilitating health care professionals and patients in optimizing a living care path according to an embodiment of the present disclosure.

In reference to FIG. 1, FIG. 2, and FIG. 10, the patient 231 uses the application 238 to register an account at step 302 which establishes communication between one or more computing devices 110, 111, 112, 113, 231c, 240 and the computing system 210 as well as assigns a unique identifier to the patient in the system. The patient and/or an HCP then enters medical history and current symptoms. In some embodiments medical history can be obtained using digital (e.g. electronic medical records, electronic health records, etc.) or paper records, as well as information obtained through word of mouth. In various embodiments symptom information can be obtained by the patient entering information, and/or can be obtained using sensors connected to one or more computing devices. In various embodiments, the system 210 obtains information by searching one or more databases 121.

The computing system 210 then uses the data obtained in step 303 to pull all known information pertaining to the causes of the symptoms in step 304. In various embodiments the computing system 210 uses internal and external data sources to gather treatment options and success statistics for options for the patient. In some embodiments the data sources can be compiled of past treatments the patient has received for the current symptoms, past treatments for all patients in a database, and/or electronically available articles and/or publications relating to the symptoms and treatment thereof.

At step 305, the computing system analyzes the data and suggests an HCP and/or a living care path. In some embodiments, the computing system uses one or more of a care path decision tree, pre-loaded options, machine learning, random forest operation, recurrent neural network, and/or AI to perform data analysis and determine a living care path and/or HCP. In various embodiments, the information pulled by the computing system at steps 303 and/or 304 are used in the analysis and suggestion process 305.

An HCP views the suggested living care path on an HCP dashboard (not shown) displayed by the application 238 on a computing device, such as 113 for example, at step 306. In some embodiments, the HCP dashboard includes patient information such as name, location, health data, and/or any other patient related data. In various embodiments, the HCP dashboard displays HCP information such as patient use, patient engagement, payment information, computing system performance, needed deficits to receive reimbursement, clinical alerts, treatment statistics, communications, and/or any other information used in medical treatment. One of ordinary skill in the art will recognize that any other suitable information can be displayed on an HCP dashboard.

After viewing the dashboard, the HCP then decides if the suggested living care path needs an adjustment. If the answer is yes, the HCP may modify the living care path at step 308 before making the path available to the patient on a patient dashboard at step 309. If the answer is no (which can be determined by either acknowledging no or letting a pre-determined default review time expire), the living care path provided by the computing system 210 is accepted and the method proceeds to step 309 without further modification.

At step 309 the patient reviews the living care path on a patient dashboard and/or HCPs can review the living care path with the patient. In some embodiments, the patient dashboard includes patient information such as name, location, time-based measures, predicted outcome, threshold goals for projected success, and/or symptoms, for example. In various embodiments the patient dashboard displays information such as payment information, appointment times, alerts, warnings, news and articles, communications, comparisons to any other cohorts (similar, different, etc.), comparisons to living care path and current patient performance, health data plotted longitudinally, and the like. One of ordinary skill in the art will recognize that any other suitable information can be displayed on a patient dashboard. In some embodiments the patient dashboard additionally displays the same information provided by HCP dashboard. In some embodiments the patient dashboard and HCP dashboard are the same dashboard.

The next step in the exemplary embodiment 300 is determining whether the living care path involves peer pairing 260 at step 310. If the answer is yes, then peer pairing is performed at step 311 before proceeding to step 312. If the answer is no, the method proceeds directly to step 312. Peer pairing is described in greater detail in FIG. 11. In some embodiments peer pairing has one or more of the computing system, HCP, or patients determining suitable partner to help ensure goals are met. In some embodiments pairing 260 involves pairing the patient with one or more of a patient with similar symptoms, a patient with a similar living care path, a patient with similar health data (e.g. biometric, physiologic, co-morbidities, etc.), social conditions (e.g., living arrangements, job requirements, care-giver responsibilities, etc.), and/or a HCP with knowledge of the medical condition or living care path contents. One of ordinary skill in the art will recognize that the patient can be paired with any person or system that can assist in the patient achieving their health care goals.

The intelligent medical care path system 100 then uses a computing device and/or medical monitoring device to collect and store medical data at step 312. The medical data collected is specified by the living care path. In some embodiments, the computing device or medical monitoring device can be one or more of fixed, portable, wearable, implanted, and/or remote (e.g., an image capturing device attached to a structure). In some embodiments the computing system accepts medical data that is manually entered.

At step 313 the computing system 210 compares the medical data collected from step 312 to one or more goal and outcome thresholds to determine if any action is needed. In some embodiments, a threshold sets points for health data (e.g. biometric, physiologic, co-morbidities, etc.) collected by a computing device. Exemplary health data (e.g. biometric, physiologic, co-morbidities, etc.) thresholds can be represented by heart rate, temperature, and/or any health data or measure (e.g. biometric, physiologic, co-morbidities, etc.) used to populate the living care path. In some embodiments, a threshold such as goals, milestones, and/or floor/ceiling levels indicating possible concerns for action are set forth in the living care path. One of ordinary skill would appreciate that a threshold can be set for any parameter.

At step 314, the computing system takes data from steps 312 and 313 and performs analysis to determine if the living care path is meeting expectations. In some embodiments the analysis is performed at one or more of the following times when medical data is received: immediately, at specified time intervals, at random time intervals, at intervals specified by the living care path, at intervals specified by the HCP, and/or at any time where health care data is needed to evaluate the patient. In some embodiments, the analysis involves using peer pairing information. In some embodiments, the analysis involves processing the inputs through a recurrent neural network, regression equations, random forest operation, machine learning, or AI program to determine which measures and individual features lead each specific person type to the most ideal outcomes. In some embodiments, analysis involves suggesting an improved living care path.

The living care path is evaluated by one of the computing system(s) 210 and or HCP at step 315. If no living care path adjustment is needed the current living care path continues. If the living care path does need adjustment the HCP can or cannot modify the living care path at step 316 or can choose to auto-accept recommendations. In some embodiments modifying the living care path can be made of one or more goals of using the computing system's suggested improved living care path, by creating a new living care path that disregards the computing system's suggestions, and/or using a combination of one or more of the computing system 210 improved living care path suggestions and one or more HCP inputs to create a new hybrid living care path.

The modified living care path is then made available on the patient dashboard at step 317. The patient either reviews the new living care path or an HCP reviews with them, and then follows any new instructions. In some embodiments, new instructions are made of one or more of contacting the HCP (physical, virtual, telehealth, etc.), adjusting behavior (exercise, number of steps, physical therapy, weight measurement frequency, etc.), making appointments with the HCP, inputting additional information, purchasing additional equipment, making payments, and/or any other instructions deemed to benefit the treatment of the patient.

Peer pairing involves connecting patients with similar medical conditions or treatment measures in an effort to provide a support base to help patients achieve their goals. In various embodiments, the system uses big data analytics to expand past a HCPs peripheral pool of patients to increase the sample size for potential peer pairing for not only the medical condition, but for personalities, social and biometric backgrounds as well. This ensures the highest probability that peers will continue to motivate each other and hold each other accountable.

Figure 11:
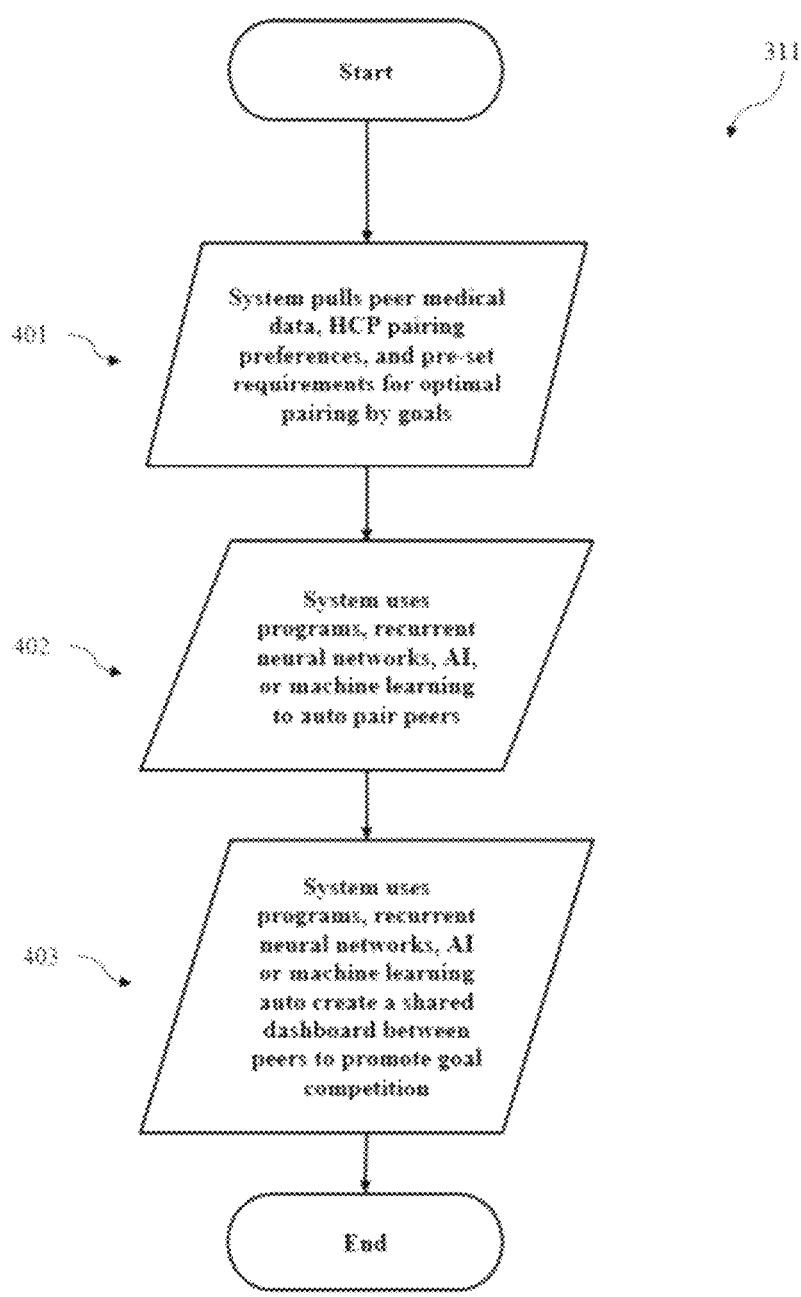
FIG. 11 depicts a flowchart representing the peer pairing step 311 according to an embodiment of the present system.

FIGS. 10-11 depicts a flowchart representing the peer pairing step 311 in FIG. 10 according to an embodiment of the present system. In this embodiment, peer pairing starts with the computing system 210 pulling one or more of peer medical data, HCP pairing preferences, requirements for optimal pairing by goals, and/or any other data needed to establish a peer pairing match. Peers can also include family members or caregivers elected by Patient as approved for varying access (view-only, interactive comments, etc.)

The computing system 210 then uses manual inputs, programs, random forest operations (described further below), AI, or machine learning to auto pair peers at step 402. In step 403, the computing system 210 uses programs, random forest operations, AI, or machine learning create a shared dashboard between patient and peer(s). In some embodiments the computing system 210 notifies one or more of the patients and/or peer(s) of the pairing. In some embodiments the computing system 210 allows communication between the patient and peer(s). In some embodiments the computing system 210 allows the patient and one or more peers to share all or some of the information on each other's dashboards. In some embodiments, the shared dashboard promotes goal competition.

In various embodiments, the system includes a dashboard to display relevant information to the patient and the HCP. In some embodiments the dashboard is a simple list of text. In other preferred embodiments, the dashboard includes modules depicting visual graphics and/or text with relevant health, education, performance, and/or other data—exemplified in FIG. 9. In some embodiments, the dashboard is completely customizable and interactive, allowing each module to be moved and arranged as the user desires.

In some respects, the system presents suggestions for language and additional requirements for reimbursement forms (explained in greater detail below), for example. In some embodiments, the HCP dashboard allows the HCP to perform virtual checkups on the patient from a remote location, supply medication as a pharmacist, either in response to and/or as a supplement to the system's continuous monitoring.

In some embodiments, the dashboard assists the HCP with planning and/or scheduling. For example, the dashboard can display a list of patients that have appointments and/or need attention for the day. The system can proactively adjust the HCP provider's priorities to streamline efficiency, all backed by analytics and big data showing the changes that have been made and the improvements that result.

Figure 12:
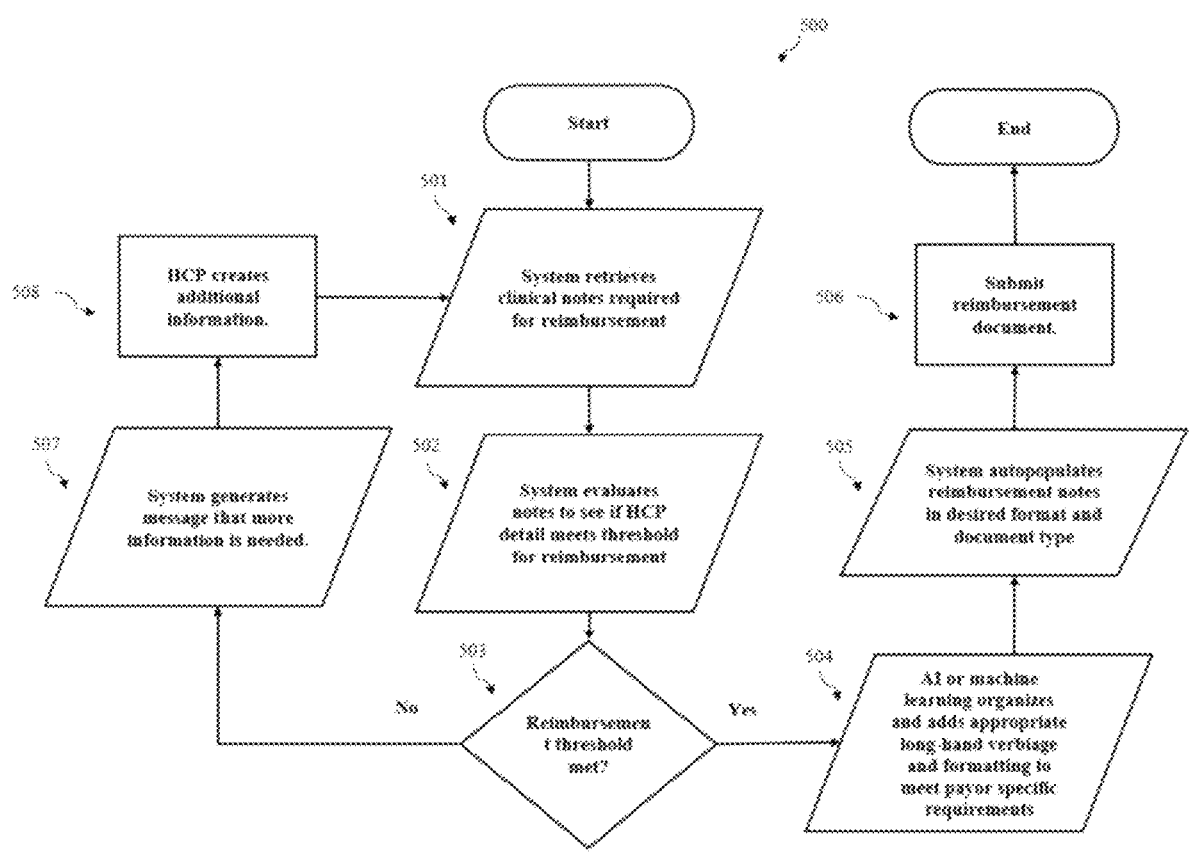
FIG. 12 shows an exemplary method for automatically populating patient healthcare and treatment information for reimbursement processing according to an embodiment of the present disclosure.

FIG. 12 shows an exemplary method for automatically populating patient healthcare and treatment information for reimbursement processing according to an embodiment of the present disclosure. Computing system 210 also included an HCP reimbursement application 500. An exemplary reimbursement application method embodiment is depicted in the FIG. 9 flowchart. At step 501, the computing system 210 retrieves all clinical notes relating to patient and/or living care path. In some embodiments the notes are made of one or more of hand written notes that have been scanned, notes entered into standard forms, notes provided by the patient, notes created by the computing system 210 while performing the method 300, and/or any other data required by a payer. In some embodiments, a payer is one or more of an insurance company, business, financial intuition, and/or any source of financial compensation.

At step 502, the computing system 210 evaluates the notes to see if all required information is present. In various embodiments evaluating can be defined by the use of random forest operations, AI, and/or machine learning to determine if a reimbursement threshold has been met at step 503. If the reimbursement threshold has not been met, the system notifies the HCP that more information is needed at step 507. The HCP inputs additional information into the computing system 210, and then the application 500 begins again at step 501.

If the reimbursement threshold has been met, random forest operations, AI and/or machine learning organizes and adds appropriate long-hand verbiage and formatting to reimbursement forms to meet payor specific requirements. The computing system 210 then auto populates reimbursement notes in a desired format and/or document type at step 505. The HCP then submits the reimbursement document to the payor at step 506. In various embodiments, the reimbursement application 500 can be integrated into an embodiment such as the one shown in FIG. 8 at any time where payment for services is needed or desired.

While the presently disclosed embodiments have been described with reference to certain embodiments thereof, it should be understood by those skilled in the art that various changes can be made and equivalents can be substituted without departing from the true spirit and scope of the presently disclosed embodiments. In addition, many modifications can be made to adapt to a particular situation, indication, material and composition of matter, process step or steps, without departing from the spirit and scope of the present presently disclosed embodiments. All such modifications are intended to be within the scope of the claims appended hereto.

Further, it is to be understood that the system is not limited in its application to the details of construction and the arrangement of components set forth in the description or illustrated in the drawings. The system is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. A method for executing a patient's living care path based on continuous monitoring of a patient comprising:

providing a non-transitory computer-readable medium storing instructions that, when executed on a computing device, cause the computing device to perform a method for executing a patient's living care path, wherein the computing device is a patient specific hub apparatus comprised of: an at least one data input device, a display; and a housing defining a cavity comprised of a medicine storage apparatus, a processor operably coupled to a memory and a power source, wherein the memory stores computer executable instructions and a processor that executes the instructions to cause the patient hub apparatus to perform the steps of:

continuously monitoring the patient by receiving patient data from a medical monitoring device to form a plurality of medical data sets;

aggregating the plurality of medical data sets using a clustering algorithm into one or more phenotypic groups to assign the patient to an at least one phenotypic group;

first processing the plurality of medical data set of the at least one assigned phenotypic group to predict one or more patient outcomes;

wherein said first processing comprises the steps of:

plotting the data inputs per patient within their phenotypic group into tables based on the total number of respective outcome possibilities to create a phenotypic group outcome data table plot;

creating a bootstrapped data table plot by randomly selecting patient data groups;

forming a new data table plot; and executing a decision tree creation from each of these bootstrapped data tables selecting an output of one or more patient outcomes;

second processing the plurality of medical data set of the assigned phenotypic group to determine an optimal time-based set of measures for increasing the probability of attaining an at least one living care path goal;

wherein said second processing comprises the steps of:

plotting the data inputs per patient within their phenotypic group into tables based on the total number of respective goals to create a phenotypic group goal data table plot;

selecting an output of the probability of attaining an at least one living care path goal;

combining an output of said one or more patient outcomes with an output of said optimal time-based set of measures to provide the living care path;

graphically displaying the living care path, and dispending medicine from said medicine storage apparatus of said patient hub in response to continuous monitoring of said patient.

2. The method of claim 1 further comprising the step of:

collecting and aggregating medical information and demographics information for a plurality of persons from one or more data sources;

analyzing the aggregated information to identify persons having similar demographics and suffering from similar medical conditions; and connecting the persons with similar diseases, disease states, social conditions, demographics and/or are suffering from similar medical conditions to facilitate a support system to achieve health care goals.

3. The method of claim 1, wherein the patient hub apparatus performing the step of receiving patient data from one or more data sources, wherein at least one data source is a medical device, wherein the medical device is chosen from the group consisting of: a watch, weight scale, blood pressure cuff, pulse oximeter, electrocardiogram, urinalysis, dynamometer, heart rate monitor, spirometer, respiration monitor, sleep tracker, and pedometer; a blood glucose meter; a pacemaker; a blood pressure monitor; an insulin pump; a pulse oximeter; a hotter monitor; an electrocardiograph; an electroencephalograph; a blood alcohol monitor; an alcohol breathalyzer; an alcohol ignition interlock; a respiration monitor; an accelerometer; a skin galvanometer; a thermometer; a patient geolocation device; a scale; an intravenous flow regulator; a patient height measuring device; a biochip assay device; a monitor for biological agents; a hazardous chemical agent monitor; an ionizing radiation sensor; a sphygmomanometer; a loop recorder; a spirometer; an event monitor; a prothrombin time (PT) meter; an international normalized ratio (INR) meter; a tremor sensor; and a defibrillator.

4. The method of claim 1, comprising the step of:

graphically displaying a differential between the living care path and present performance, a plurality of measures to alter this differential, and at least one predicted outcome on said patient hub.

* * * * *